United States Patent [19]

Evers

[11] 4,235,889
[45] Nov. 25, 1980

[54] THERAPEUTIC AGENT FOR THE EXTERNAL TREATMENT OF PSORIASIS, TINEA AND ECZEMAS

[75] Inventor: Walter Evers, Pinneberg, Fed. Rep. of Germany

[73] Assignee: Pharmazeutische Fabrik Evers & Co., Pinneberg, Fed. Rep. of Germany

[21] Appl. No.: 33,154

[22] Filed: Apr. 25, 1979

Related U.S. Application Data

[63] Continuation-in-part of Ser. No. 757,620, Jan. 7, 1977, abandoned.

[51] Int. Cl.³ .............................................. A61K 35/78
[52] U.S. Cl. .................................... 424/195; 424/312; 424/365
[58] Field of Search ........................ 424/195, 312, 365

[56] References Cited

U.S. PATENT DOCUMENTS 228,026   5/1880   Berger .................................. 424/195

OTHER PUBLICATIONS

Merck Manual–10th Ed., 1961, pp. 1472–1474.
Sagarin–Cosmetics Science & Technology (Textbook), pp. 91–93, 106, 115–117 (1957).
Remington's Pharmaceutical Sciences–13th Ed., p. 853 (1965).
Merck Index, 9th Ed., p. 707 (1976).

Primary Examiner—Leonard Schenkman
Attorney, Agent, or Firm—Gordon W. Hueschen

[57] ABSTRACT

The subject of the invention is a pharmaceutical composition for the external treatment of psoriasis, tinea and eczemas, comprising coconut oil, palm kernel oil, an extract of *Laurus nobilis* (Linn.) and an emulsifier.

12 Claims, No Drawings

THERAPEUTIC AGENT FOR THE EXTERNAL TREATMENT OF PSORIASIS, TINEA AND ECZEMAS

CROSS REFERENCE TO RELATED APPLICATION

This application is a continuation-in-part application of my prior-filed copending application, Ser. No. 757,620, filed Jan. 7, 1977, now abandoned.

BACKGROUND OF THE INVENTION

1. Field of the Invention

The object of the present invention is to provide a pharmaceutical composition for the external treatment of psoriasis, tinea and eczemas, with which treatment on humans has proved very successful. Even "hopeless cases" have shown distinct healing. A further object of the invention is that the composition for topical application makes possible a therapy which is free from side effects.

2. Prior Art

Therapeutic agents which are known for the external treatment of psoriasis, tinea and eczemas have not yet proved sufficiently effective, so that topical ointments based on tars have frequently been used in combination with an X-ray treatment.

SUMMARY

The subject of the invention is a pharmaceutical composition for topical application for the external treatment of psoriasis, tinea and eczemas, which comprises 30 to 50 percent by weight of coconut oil, 30 to 50 percent by weight of palm kernel oil, 5 to 15 percent by weight of laurel oil from *Laurus nobilis* (Linn.), and 5 to 15 percent by weight of an emulsifier, the percentages by weight summing up to 100 percent by weight.

In one embodiment of the composition of the invention, it may contain wool fat as emulsifier.

In another embodiment, the composition may contain wool wax alcohols as the emulsifier.

In a further embodiment, the composition may contain salts of pharmacologically permissible metals of aliphatic monocarboxylic acids with 10 to 22 carbon atoms as the emulsifier.

In an additional embodiment, the composition may contain mono- and/or di-glycerides of aliphatic monocarboxylic acids with 10 to 22 carbon atoms as the emulsifier.

In still an additional embodiment, the composition may contain about 50 percent by weight of coconut oil, 30 percent by weight of palm kernel oil, 10 percent by weight of laurel oil, and 10 percent by weight of wool fat.

In a further embodiment, the composition contains about 40 percent by weight of coconut oil, 40 percent by weight of palm kernel oil, 10 percent by weight of laurel oil, and 10 percent by weight of zinc stearate.

In a still further embodiment, the composition contains about 50 percent by weight of coconut oil, 30 percent by weight of palm kernel oil, 10 percent by weight of laurel oil, and 10 percent by weight of zinc stearate.

In still an additional embodiment, the composition contains about 30 percent by weight of coconut oil, 50 percent by weight of palm kernel oil, 10 percent by weight of laurel oil, and 10 percent by weight of zinc stearate.

In another embodiment, the pharmaceutical composition contains small amounts of antioxidants.

In yet another embodiment, the pharmaceutical composition contains small amounts of preservatives.

Coconut oil is isolated from the fruit of the coconut palm (*Cocos nucifera*) and contains, as the main constituents, 50 to 60% of caprilolauromyristin and 15 to 20% of myristodilaurine. In addition it contains small amounts of oleic acid glycerides, palmitodimyristine and stearodipalmitine. With reference to the fatty acid composition (in percentage) of coconut oil, *Ullmanns Encyklopadie der technischen Chemie* (*Ullmans Encyclopedia of Technical Chemistry*), 4th Edition, Volume 11 gives, on pages 458 and 459, 13 percent of $C_{10}$ and lower saturated fatty acids, 45 to 50 percent of $C_{12}$ saturated fatty acids, 8 to 9 percent of $C_{16}$ saturated fatty acids, and 2 to 3 percent of $C_{18}$ saturated fatty acids, traces of $C_{14/1}$ unsaturated fatty acids, traces of $C_{16/1}$ unsaturated fatty acids, 5 to 8 percent of $C_{18/1}$ unsaturated fatty acids, and 1 to 3 percent of $C_{18/2}$ unsaturated fatty acids. The content of free fatty acids in coconut oil is 5 to 17 percent (calculated relative to oleic acid). Coconut oil, as used in this specification, is also designated coconut fat or coconut butter, both in the literature and in commerce. It is preferred that the coconut oil employed be natural, but synthetic coconut oil prepared in accordance with foodstuff technology can also be used for the present invention.

According to the citation, in Ullmanns on pages 458 and 459, palm kernel oil contains, with reference to the fatty acid composition (in percentage), 7 percent of $C_{10}$ and lower saturated fatty acids, 47 to 52 percent of $C_{12}$ saturated fatty acids, 16 percent of $C_{14}$ saturated fatty acids, 6 to 9 percent of $C_{16}$ saturated fatty acids, 2 to 3 percent of $C_{18}$ saturated fatty acids, 10 to 18 percent of $C_{18/1}$ unsaturated fatty acids, and 1 to 3 percent of $C_{18/2}$ unsaturated fatty acids. Palm kernel oil contains 0.4 to 9.8 percent of free acids.

In its properties and characteristic values, palm kernel oil is very similar to coconut oil; however, compared with the latter, it contains more oleic acid and only half as much $C_8$ and $C_{10}$ fatty acids in its glycerides. The palm kernel oil glycerides consist of 60 to 65 percent of tri-saturated components, about 25 percent of disaturated-monounsaturated components, and 10 to 15 percent of monosaturated-diunsaturated components. Palm kernel oil, as used in this specification, is also designated palm kernel fat in the literature and in commerce. It is preferred to use natural palm kernel oil, but synthetic palm kernel oil prepared in accordance with foodstuff technology can also be used for the present invention.

"Laurel oil", as used in this specification, is understood to be the product "Oleum Lauri" described on pages 470 to 471 of the *Deutsches Arzneibuch 6* (*German Pharmacopoeia*, 6th Edition), that is to say, the yellow-to-green semi-solid mixture of fats and oils, and lipid compositions expressed from the fruits of *Laurus nobilis* (Linn.) using heat or isolated by boiling. Laurel oil melts at approximately 36° C. to give a dark green liquid which has a spicy odor and a bitter taste and mainly consists of lauryl laurate, lauryl stearate, and the essential oils and lipid components.

The laurel oil described above is also occasionally known as "laurel tallow" in the literature and in European commerce. It is a greenish fatty composition which is isolated from the fresh fruits of the laurel (*Laurus nobilis* (Linn.)). The density is approximately 0.88, the melting point is about 40° C., the saponification number is 198-199, and the iodine number is 68-80. Each of "laurel oil" and "laurel tallow", as defined in *Deutsches Arzneibuch* 6, and as defined above, may be used in the practice of this invention.

Yet a further embodiment of the novel compositions of the invention comprises a composition in which the laurel essential extract consists of a mixture of 50 to 100 percent by weight of "laurel tallow" and 50 to 0 percent by weight of "laurel oil", as the terms are used in literature and commerce.

As used in this specification, laurel oil is defined as a mixture of fats, oils, and lipid components which is isolated from the leaves and berries of laurel, i.e., the plant *Laurus nobilis* (Linn.), and is a pale yellow oil which has a spicy odor and contains about 50 percent of cineol, as well as α-pinene, linalool, citral, geraniol, eugenol, and hitherto unidentified substances. In the *Merck Index*, 9th Edition (1976), page 707, No. 5228, there is defined: "*Laurel Oil.* Laurel berry oil. Fixed oil from fresh fruit of *Laurus nobilis* L., *Lauraceae. Constit.* Chiefly the lauryl alcohol esters of lauric, stearic, etc. acids and a volatile oil, the so-called laurel camphor. Greenish, fatty solid; the green color due to presence of some chlorophyll. d about 0.88. mp about 40°. $n_D^{25}$ 1.4783. Sapon No. 198-199. Iodine No. 68-80. Insol in water; sparingly sol in alcohol; sol in benzene, ether, carbon disulfide."

The term "laurel camphor" for the volatile oil defined in the Merck Index definition of "Laurel Oil" is not identical with Camphor USP, which is a solid ketone of the formula $C_{10}H_{16}O$ which is isolated from the plant *Cinnamomum camphora* (Linn.), or the synthetic isomorph thereof defined in *Remington's Pharmaceutical Sciences*, 13th Edition, page 813 (1965). The volatile oil defined as laurel camphor in the *Merck Index* and the solid substance (Camphor USP) are very different things and are not to be confused. In the practice of the invention of this specification, no Camphor USP is contained in "laurel oil" or "laurel tallow". Camphor USP is neither found in nor contemplated as a component of the instant novel compositions.

It is readily apparent that the "laurel oil" of the *Merck Index* definition is identical with the "laurel tallow" of European literature and commerce, and that the "laurel oil" of European literature and commerce is the "laurel oil" of the *Merck Index* definition enriched or more concentrated in the more volatile, lower-melting fats, essential oils, and lipid components. As used in this specification, "laurel oil" differs from "laurel tallow" in a composition sense solely in that the former contains somewhat more of the volatile components than does the latter, which latter is somewhat richer in the higher-melting lauryl alcohol esters of lauric and longer-chain fatty acids. Both "laurel oil" and "laurel tallow" derive from the same biological source, i.e., the fruits and leaves of *Laurus nobilis* (Linn.).

In the sense of this invention, emulsifiers are defined as those which are pharmacologically and physiologically tolerated by the diseased skin surface to be treated and which impart a favorable consistency to the compositions hereof for their topical application to the skin, and which facilitate the taking up of the therapeutic agent by absorption and/or resorption and/or persorption.

Suitable emulsifiers and emulsifying mixtures which meet these requirements are known to those skilled in the art and are set forth, for example, in the book Römpp, *Chemie Lexikon (Chemical Dictionary)*, 6th Edition, 1966, Volume I, columns 1799 to 1806, along with further literature references and a list of suppliers.

Examples of emulsifiers which can be used are: wool fat, wool wax alcohols, salts of pharmacologically permissible metals with aliphatic monocarboxylic acids with 10 to 22 carbon atoms, such as calcium stearate, magnesium stearate, aluminium stearate or zinc stearate, and emulsifier mixtures of mono- and/or diglycerides of aliphatic monocarboxylic acids with 10 to 22 carbon atoms.

The compositions of the invention can also contain small amounts of antioxidants to prevent oxidative destruction of those components of the composition susceptible thereto. Antioxidants and their use are described in the chapter "Antioxidantien" ("Antioxidants") in Volume 8 of *Ullmanns Encyklopadie der technischen Chemie (Ullmanns Encyclopedia of Technical Chemistry)*, 4th Edition. The compounds in the table below have been found effective as antioxidants in the practice of this invention, and are listed therein together with their customary range of incorporation, in percentage by weight, relative to the total weight of the composition. In addition, compounds which function as synergists to the antioxidants are also set forth in the table.

| Antioxidants | % by weight |
| --- | --- |
| L-Ascorbic acid | 0.03-0.20 |
| 2-/3-tert.-butyl-4-hydroxy-anisole (BHA) | 0.005-0.02 |
| 2,6-di-tert.-butyl-4-hydroxy-toluene (BHT) | 0.005-0.12 |
| alkyl gallates | |
| alkyl = $C_3H_7$(PG), $C_8H_{17}$(OG) or $C_{12}H_{25}$(DG) | 0.008-0.10 |
| nordihydroguaiaretic acid (NDGA) | 0.005-0.025 |
| 3,3'-thio-dipropionic acid | 0.01-0.02 |
| 3,3'-thio-bis-(propionic acid alkyl esters) | |
| alkyl = $C_{12}H_{23}$(DLTDP) or $C_{18}H_{37}$(DSTDP) | 0.01-0.09 |
| Tocopherols | 0.01-0.30 and more |
| 2,4,5-trihydroxy-butyrophenone (THBP) | 0.01-0.02 |
| ascorbic acid esters, for example, ascorbic acid myristate, ascorbic acid palmitate or ascorbic acid stearate | 0.01- 0.015 |
| Synergists: | |
| L-Ascorbic acid, lecithin, phosphoric acid, polyphosphoric acid, tartaric acid and citric acid | |

The pharmaceutical compositions of this invention can also contain small amounts of preservatives to prevent microbiological degradation. Preservation by chemical agents is described on pages 440 to 461 in Volume 11, 1960, of *Ullmanns Encyklopadie der technischen Chemie (Ullmanns Encyclopedia of Technical Chemistry)*, 3rd Edition. Examples of preservatives effective in the practice of this invention are methyl p-hydroxy benzoate, ethyl p-hydroxy benzoate, propyl p-hydroxy benzoate, and sorbic acid. In general, the addition of about 0.01 to 0.2 percent by weight of preservative, relative to the weight of the total composition, suffices to prevent growth of molds, yeasts and bacteria and consequent spoilage and loss of efficacy of the compositions. A particularly useful preservative consists of seven parts of methyl p-hydroxy benzoate and three parts of propyl p-hydroxy benzoate, which mixture is effective at a total amount of 0.1 percent by weight, relative to the weight of the total composition.

The topical pharmaceutical compositions of this invention can be manufactured using customary methods of the pharmaceutical compounding art. Thus, the components can be brought into the mobile or fluid state by careful warming to about 35° to 50° C. and combined by stirring, the emulsifier or emulsifier mixture then being added and finely dispersed.

If desired, a completely homogeneous spreadable product can be manufactured by processing the batch produced in this way in a homogenizer, in which the batch is forced through nozzles under high pressure.

If the product has become highly viscous due to storage at low temperatures, or if it should be found to contain crystalline fractions, it can be restored to a state in which it is very readily spreadable by gentle warming to about 30° C.

Psoriasis is a disease for which there has been no satisfactory method of treatment to date. The cause of psoriasis is unclear, but genetic factors appear to play a major role.

The therapeutic composition of the invention is a combination of active compounds which is novel for the treatment of psoriasis and represents a therapy free from side effects. Excellent therapeutic results have been achieved in preliminary medical tests, even in "hopeless cases".

By penetrating into the diseased tissue, the active components of the compositions herein apparently produce necrosis of the infected cells, which is apparent in the form of dermal shedding around the areas of erythematous development. The efficacy of the compositions is also demonstrated by the fact that no punctiform hemorrhages occur. After topical application to the effected sites, a gratifying alleviation of the irritating itching is noticeable after a few days.

In the initial stages of treatment, visible reddening of the skin areas which are regenerating usually arises as a result of increased blood flow.

The treatment period varies from individual to individual. Diseases in the primary stages require a considerably shorter period to demonstrate beneficial results (six to eight weeks). Despite reddening of the skin, the treatment can be continued until a normal skin color and gross appearance have returned to the affected site.

The fields of efficacy for the novel compositions comprise the topical treatment of psoriasis, tineas, and eczemas; the treatment is indicated in particular in the case of chronic diseases.

Unless otherwise prescribed by the doctor, the composition of the invention may conveniently and effectively be applied, or lightly rubbed into the affected areas of the skin three times a day. The treatment can be continued for a prolonged period without hesitation, or the development of distressing side effects.

After the composition has been topically applied, all contact with water should preferably be avoided for a period of at least thirty minutes.

It is appropriate to carry out the treatment with the compositions of the invention under medical supervision.

No side effects, concomitant symptoms, contra-indications, or risks have become known to date.

The following tests have been carried out to prove the therapeutic effectiveness of the compositions of the invention.

TEST 1

Skin compatibility of coconut oil, palm kernel oil, and emulsifier on the healthy skin In the first instance, compatibility tests were carried out on the healthy skin of forty voluntary persons, consisting of twenty men and twenty women of 21 to 70 years of age. By these investigations it was confirmed that coconut oil, palm kernel oil, and the emulsifiers mentioned in this application, as sole substance or in combination one with the other, are tolerated without irritation on the healthy skin.

These personal investigations and results are in agreement with the results of examinations of the manufacturers.

TEST 2

Skin compatibility test of laurel oil, melting point 36° C., and laurel oil (laurel tallow), melting point 40° C., on the healthy skin The same forty persons were used for this test. Laurel oil (or laurel tallow) was applied and rubbed in in the liquid state in small amounts of 50±5 mg. After thirty minutes, the treated skin was observed. In sixteen men and seventeen women slight reddening of skin with the feeling of slight manifestation of irritation was observed.

After thirty minutes, 50±5 mg laurel oil was again applied to the skin of fifteen men and sixty minutes later, a very distinct itching irritation with reddening had occurred with nine men, and for six men formation of pustules, reddening and itching irritation had set in.

After 24 hours, one man complained of allergic malady.

These investigations have shown that laurel oil (or laurel tallow) applied alone on the healthy skin produces appearance of irritation.

TEST 3

Skin compatibility tests of therapeutic agents according to this application on the healthy skin 30 to 50 percent by weight of coconut oil,
30 to 50 percent by weight of palm kernel oil,
5 to 15 percent by weight of laurel oil,
5 to 15 percent by weight of emulsifier.

The agents used in these tests were manufactured according to Examples 1 to 77 following. The same forty persons were used as in the previous tests. Surprisingly, good compatibility of the compositions appeared with the healthy skin.

TEST 4

Skin compatibility tests of laurel oil, melting point 36° C., and laurel oil (laurel tallow), melting point 40° C., on the ill skin (psoriasis, tinea and eczemas)

These examinations were carried out as described under Test 2, but there was proved the reaction on the ill skin of (a) six men—illness: psoriasis
(b) two men and two women—illness: tinea
(c) four men and one woman—illness: eczema.

Four men of group (a), two men and one woman of group (b), and three men and one woman of group (c) had noted a strong burning pain upon application. The four men of group (a) tried spontaneously to wipe the test substance off their skin. Inflammation focus, perceived as point of pain and burning, appeared at two men of group (a), one woman of group (b), and one man of group (c) in the course of fifteen minutes.

These tests show that laurel oil and laurel tallow, with melting points of 36° C. and 40° C. respectively, are not compatible on the skin diseased with psoriasis, tinea and eczemas; moreover, skin irritation is produced. That is the reason that these substances cannot be used as therapeutic agents alone.

TEST 5

Skin compatibility tests of therapeutic agents according to the present invention on the skin diseased with psoriasis, tinea and eczemas For these tests there were used agents, manufactured according to Examples 1 to 77. These examinations were carried out as described under Test 2, evaluating the reaction on the ill skin of:
(a) six men and four women—illness: psoriasis
(b) four men and four women—illness: tinea
(c) four men and two women—illness: eczema.

In a completely concordant manner, no skin irritation or risk factor was determined.

TEST 6

Therapeutic examination on the skin, diseased with psoriasis, tinea and eczemas

The skin, diseased with psoriasis, tinea and eczemas of the test persons who placed themselves at the disposal, for the skin compatibility tests of therapeutic agents according to the present invention, was proved with the following combinations:

I.

45 percent by weight of coconut oil
45 percent by weight of palm kernel oil
10 percent by weight of emulsifier

II.

80 percent by weight of coconut oil
10 percent by weight of laurel oil
10 percent by weight of emulsifier

III.

80 percent by weight of palm kernel oil
10 percent by weight of laurel oil
10 percent by weight of emulsifier

IV.

30 to 50 percent by weight of coconut oil
30 to 50 percent by weight of palm kernel oil
5 to 15 percent by weight of laurel oil
5 to 15 percent by weight of emulsifier.

The combination I, II, III, and IV were applied on and lightly rubbed into the skin at different sites of the same person, three times daily.

Combination I did not show any effect after six weeks.

The combinations II and III, in comparison with combination I and with the untreated skin, showed a small therapeutic, but not sufficient, effect after six weeks.

Upon examination of combination IV according to the invention, after six weeks, in all cases good therapeutic results were confirmed.

As experience and the test results have shown, the therapeutic effects are obtainable only with a composition made according to the present invention.

Further, the following additional tests were carried out to prove effectiveness of the therapeutic combination of the present invention.

TEST GROUPS (A)

Forty people, twenty male, twenty female, in the age group 21 to seventy, free from skin diseases.

(B)(a)

42 people, 22 male, twenty female, suffering from chronic psoriasis, age group 18 to 45.

(b)

Eight people, four male, four female, suffering from tinea, age group 30 to 42.

(c)

Twelve people, four male, eight female, suffering from eczema, age group 27 to 36.

(C)(a)

114 people, fifty male, 64 female, suffering from chronic psoriasis, age group 18 to 63.

(b)

Twenty people, ten male, ten female, suffering from tinea, age group 25 to 42.

(c)

Twenty people, eleven male, nine female, suffering from eczema, age group 26 to 36.

Group C partially contains Group B.
All test people volunteered for the tests.

TESTED PHARMACEUTICAL COMPOSITIONS ACCORDING TO THE INVENTION (A) Forty percent coconut oil; forty percent palm kernel oil; ten percent laurel oil; 9.9 percent Ca-stearate; 0.1 percent hydroxybenzoic acid ester.
(B) Fifty percent coconut oil; fifty percent palm kernel oil; ten percent laurel oil; 0.08 percent tocopherol; 9.92 percent lanolin.
(C) Thirty percent coconut oil; fifty percent palm kernel oil; 8.4 percent laurel tallow; 3.6 percent etheral laurel oil; ten percent zinc stearate.
(D) 45 percent coconut oil; 45 percent palm kernel oil; five percent laurel oil; 0.05 percent sorbic acid; 0.015 percent ascorbic acid-palmitate; 4.935 percent wool wax alcohols.

TESTS CARRIED OUT ON HEALTHY PATIENTS (1) Skin compatibility tests of coconut oil, palm kernel oil and emulsifying agents on healthy skin:
With Test Group A, first of all compatibility tests were carried out on the healthy skin. By means of these tests it was confirmed that coconut oil, palm kernel oil and those emulsifiers named in this patent application, either as sole substance tested or in combination applied to the healthy skin, were tolerated without irritation.

Said tests and results correspond entirely with the results of the tests carried out by the various manufacturers.

(2) Skin compatibility tests of laurel oil, melting point 36° C. and laurel oil (laurel tallow), melting point 40° C., on the healthy skin.

The same forty people were used for this test.

Laurel oil or laurel tallow was applied in a liquid state in a small quantity of 50±5 mg and rubbed in.

After thirty minutes the treated skin was observed. In the case of sixteen men and seventeen women, slight skin reddening was observed along with the sensation of slight irritation.

In the case of fifteen men, a renewed quantity of 50±5 mg laurel oil was applied after thirty minutes. After sixty minutes, nine men experienced a very marked irritation together with reddening and six men experienced the formation of blisters, reddening and irritation. After 24 hours one man complained of allergic conditions.

These tests have shown that laurel oil or laurel tallow when applied alone to the healthy skin cause irritation.

(3) Skin compatibility tests of therapeutic agents, according to the invention, on the healthy skin:

Test Group A; compositions A+C.

Surprisingly enough, there was a good compatibility of the preparations on the healthy skin in the case of 39 test people. In one case (female), composition C produced a slight reddening, which was subjective but not regarded as unpleasant.

(4) Skin compatibility tests of laurel oil, melting point 36° C., and laurel oil (laurel tallow), melting point 40° C., on the diseased skin (psoriasis, tinea and eczemas). These tests were carried out as described in Test 2.

Test Groups B(a), B(b), B(c).

Twelve men and twelve women from the Group B(a), four men and two women from the Group B(b) and three men and eight women from the Group B(c) indicated a marked burning pain upon application. The four people from the Group B(a) tried immediately to rub the test substance off the skin.

In the case of eight men and nine women from the Group B(a), two women from the Group B(b) and two men from the Group B(c), focuses of inflammation occurred within the course of fifteen to thirty minutes, which were experienced as areas of pain and burning.

These tests show that laurel oil with the melting point 36° C. or 40° C. is incompatible on the skin diseased with psoriasis, tinea and eczemas, causes skin irritation and pain, and for this reason alone cannot be used as a therapeutic agent.

(5) Skin compatibility tests of therapeutic agents according to the present invention on skin diseased with psoriasis, tinea and eczemas:

Test Groups B(a), B(b), B(c); compositions A+C.

Surprisingly enough, no skin irritations or other side effects were observed in this series of tests.

(6) Therapeutic tests on skin diseased with psoriasis, tinea and eczemas:

Test Groups C(a), C(b), C(c); compositions A, B, C, D.

The compositions were applied three times daily to the test subjects on various diseased areas of the skin. For comparison, no treatment was undertaken on a fifth area of their skin, which was likewise erythematic. The patients guaranteed in writing that they would give up any further therapeutic treatment of their skin during the ten (10) week period of tests with the compositions according to the invention.

The following results were evident after treatment:

TABLE I

| Composition | Ca | | | Cb | | | Cc | | |
|---|---|---|---|---|---|---|---|---|---|
| A | 30 ♂ | 50 °+ | +++ | 2 ♂ | 4 °+ | ++ | 3 ♂ | 2 °+ | ++ |
|   | 18 ♂ | 14 °+ | ++  | 7 ♂ | 6 °+ | +  | 7 ♂ | 6 °+ | +  |
|   | 2 ♂  | 0     |     | 1 ♂ | 0    |    | 1 ♂ | 1 °+ | 0  |
|   |      | −     |     |     | −    |    |     |      | −  |
| B | 30 ♂ | 48 °+ | +++ | 2 ♂ | 3 °+ | ++ | 3 ♂ | 2 °+ | ++ |
|   | 19 ♂ | 15 °+ | ++  | 7 ♂ | 6 °+ | +  | 7 ♂ | 7 °+ | +  |
|   | 1 ♂  | 1 °+  | 0   | 1 ♂ | 1 °+ | 0  | 1 ♂ |      | 0  |
|   |      | −     |     |     | −    |    |     |      |    |
| C | 30 ♂ | 48 °+ | +++ | 2 ♂ | 3 °+ | ++ | 3 ♂ | 2 °+ | ++ |
|   | 19 ♂ | 14 °+ | ++  | 7 ♂ | 7 °+ | +  | 6 ♂ | 6 °+ | +  |
|   | 1 ♂  | 2 °+  | 0   | 1 ♂ |      | 0  | 2 ♂ | 1 °+ | 0  |
|   |      | −     |     |     | −    |    |     |      |    |
| D | + ♂  | 45 °+ | +++ | 2 ♂ | 3 °+ | ++ | 3 ♂ | 2 °+ | ++ |
|   | 18 ♂ | 14 °+ | ++  | 7 ♂ | 6 °+ | +  | 7 ♂ | 7 °+ | +  |
|   | 2 ♂  | 5 °+  | 0   | 1 ♂ | 1 °+ | 0  | 1 ♂ |      | 0  |
|   |      | −     |     |     | −    |    |     |      | −  |

Key to symbols:
++ = very marked improvement
+ = still clear improvement
0 = no noticeable reaction
− = Worsening effect.

TABLE II

| Test Group | Good Effect ++ and + | No Effect 0 and − |
|---|---|---|
| C(a) | 442 | 14 |
| C(b) | 74  | 6  |
| C(c) | 73  | 7  |

In none of the patients (except for one evident allergy to hydroxybenzoic acid esters) was there any appearance of subjective or objective side effects.

The described test results show that the desired therapeutic effects can be achieved only with a pharmaceutical composition according to the present invention.

ADDITIONAL CLINICAL EVALUATION

Further, comparative treatments of psoriatic lesions with customary therapeutic medicaments and with topical application of the composition defined below were undertaken. That composition (I) was composed of:

Coconut oil: 50 grams
Palm kernel oil: 30 grams
Laurel oil as defined in the German Pharmacopeia: 10 grams
Emulsifier of equal parts of zinc stearate and lanolin: 10 grams This composition (I) was applied topically to sixty chronic clinical psoriasis patents for evaluation. To fifteen patients, there were also applied for side-by-side comparison, preparations which, according to the art, are customary antipsoriatically effective therapeutic medicaments. Those known medications evaluated were (1) a preparation based upon corticosteroids (Triamcinolone) and (2) a tar preparation based upon coal tar.

In none of the fifteen patients under evaluation with the above compositions (1) and (2) did there occur a single exacerbation of the clinical condition compared with the control or comparative treatments.

In twelve of the fifteen patients treated for twelve to fourteen days with the above-identified inventive composition (I), there occurred a surprising objectively visible lessening of the affliction, such that the affected body areas (mostly of the elbows and in the scalp area) were rendered completely normal. This was not thought possible by the patients, who for many years had used the customary medicaments for psoriasis.

In the remaining 45 patients, no comparative therapeutic evaluation was undertaken. Each of these patients had in earlier years sought medical treatment for their affliction without any substantial improvement, although further advance of the affliction was delayed for some.

In 38 patients, there occurred within from two weeks to two months an exfoliation of the diseased dermal tissue. Also, during the post-treatment period of three to eight months, there was no further occurrence of psoriasis on the previously afflicted dermal parts of these 38 patients.

Thus the therapeutic efficacy of the compositions of the present invention has been established in comparison with treatments heretofore known, in which comparison the compositions of the invention were shown to be highly antipsoriatically effective.

The compositions of this invention are illustrated in more detail by the examples which follow by way of illustration and not by limitation.

EXAMPLES 1 to 8

Table I gives the individual components, and the amount thereof, used for Examples 1 to 8. The components were filled into a stirred kettle, the outer walls of which were heated to about 40° to 50° C. by warm water. With the aid of the stirrer, the resulting melt was mixed until completely homogeneous. After cooling to room temperature, the stirrer was switched off. The resulting composition of the invention was filled into sealable tubes holding a net weight of 30 g.

TABLE I

| Example No. | Coconut* oil | Palm* kernel oil | Laurel tallow Deutsches Arzneibuch 6 | Emulsifier |
|---|---|---|---|---|
| 1 | 500 g | 300 g | 50 g | 150 g wool fat |
| 2 | 350 g | 450 g | 75 g | 125 g wool fat |
| 3 | 400 g | 400 g | 90 g | 110 g wool fat |
| 4 | 450 g | 350 g | 100 g | 100 g wool fat |
| 5 | 410 g | 390 g | 150 g | 50 g wool fat |
| 6 | 450 g | 300 g | 150 g | 100 g wool fat |
| 7 | 400 g | 400 g | 110 g | 90 g wool fat |
| 8 | 300 g | 500 g | 100 g | 100 g wool fat |

*natural form

EXAMPLES 9 to 12

The procedure was as in Examples 1 to 8. However, the amounts and components indicated in Table II were employed.

TABLE II

| Example No. | Coconut oil | Palm kernel oil | Laurel tallow Deutsches Arzneibuch 6 | Emulsifier |
|---|---|---|---|---|
| 9 | 300 g | 500 g | 170 g | 90 g zinc stearate |
| 10 | 400 g | 400 g | 100 g | 100 g zinc stearate |
| 11 | 500 g | 300 g | 100 g | 100 g zinc stearate |
| 12 | 300 g | 500 g | 100 g | 100 g zinc stearate |

EXAMPLES 13 to 20

0.8 g of α-tocopherol was incorporated, as an antioxidant, into the formulations obtained according to Example 1 to 8.

EXAMPLES 21 to 28

0.1 g of ascorbic acid myristate, as an antioxidant, and 0.1 g of L-ascorbic acid, as a synergist, were incorporated into the formulations obtained according to Examples 1 to 8.

EXAMPLES 29 to 36

0.7 g of methyl p-hydroxy benzoate and 0.3 g of propyl p-hydroxy benzoate were incorporated, as a preservative, into the formulations obtained according to Examples 1 to 8.

EXAMPLES 37 to 44

0.7 g of methyl p-hydroxy benzoate and 0.3 g of propyl p-hydroxy benzoate were incorporated, as a preservative, into the formulations obtained according to Examples 21 to 28.

EXAMPLES 45 to 52

The procedure employed was as indicated in Examples 1 to 8. However, the constituents indicated in Table III were used.

TABLE III

| Example No. | Coconut* oil | Palm* kernel oil | Laurel tallow | Laurel oil Deutsches Arzneibuch 6 | Emulsifier |
|---|---|---|---|---|---|
| 45 | 500 g | 300 g | 25 g | 25 g | 150 g wool fat |
| 46 | 350 g | 450 g | 50 g | 25 g | 125 g wool fat |
| 47 | 400 g | 400 g | 80 g | 10 g | 110 g wool fat |
| 48 | 450 g | 350 g | 175 g | 25 g | 100 g wool fat |
| 49 | 500 g | 300 g | 100 g | 50 g | 50 g wool fat |
| 50 | 450 g | 300 g | 120 g | 30 g | 100 g wool fat |
| 51 | 400 g | 400 g | 100 g | 10 g | 90 g wool fat |
| 52 | 300 g | 500 g | 95 g | 5 g | 100 g wool fat |

*natural form

EXAMPLES 53 to 60

The procedure followed was as indicated in Examples 45 to 52, but 0.6 g of α-tocopherol was additionally incorporated as an antioxidant.

EXAMPLES 61 to 68

The procedure followed was as indicated in Examples 53 to 60, but 0.5 g of sorbic acid was additionally incorporated as a preservative. The amount of antioxidant added to the therapeutic agent of the invention can be between 0.005 and 0.4 percent by weight, depending on the nature of the antioxidant used. Any synergist can be used in the same range.

EXAMPLES 69 to 76

The procedure was as in Examples 1 to 8. However, the amounts and substances indicated in Table IV were employed.

TABLE IV

| Example No. | Coconut* oil | Palm* kernel oil | Laurel tallow Deutsches Arzneibuch 6 | Emulsifier |
|---|---|---|---|---|
| 69 | 490 g | 410 g | 50 g | 50 g wool wax alcohol |
| 70 | 420 g | 450 g | 75 g | 55 g wool wax alcohol |
| 71 | 415 g | 435 g | 90 g | 60 g wool wax alcohol |
| 72 | 470 g | 380 g | 100 g | 50 g wool wax alcohol |
| 73 | 390 g | 400 g | 150 g | 60 g wool wax alcohol |
| 74 | 440 g | 360 g | 150 g | 50 g wool wax alcohol |
| 75 | 415 g | 425 g | 110 g | 50 g wool wax alcohol |

TABLE IV-continued

| Example No. | Coconut* oil | Palm* kernel oil | Laurel tallow Deutsches Arzneibuch 6 | Emulsifier |
| --- | --- | --- | --- | --- |
| 76 | 340 g | 500 g | 100 g | 60 g wool wax alcohol |

*natural form

EXAMPLE 77

A mixture consisting of 425 g of coconut oil (natural form), 425 g of palm kernel oil (natural form), 100 g of laurel tallow, as defined in *Deutsches Arzneibuch* 6, and 50 g of emulsifier (Tegin M TM) based on a glycerol mono-/di-stearate which is related to natural fat, not self-emulsifying and has a high monoglyceride content (compare *Ullmann IV*, 29 and 34), was processed in accordance with the instructions in Examples 1 to 8 to give the composition of the invention.

It will be understood that while the invention has been described specifically with reference to certain embodiments thereof, various changes and modifications may be made, all within the full and intended scope of the claims which follow.

I claim:

1. A pharmaceutical composition for the external treatment of psoriasis, tinea and eczemas consisting essentially of thirty to fifty percent by weight of coconut oil, thirty to fifty percent by weight of palm kernel oil, five to fifteen percent by weight of an extract of the leaves and berries of laurel (*Laurus nobilis* (Linn.)) and five to fifteen percent by weight of an emulsifier, the percentages by weight summing up to 100 percent.

2. Pharmaceutical composition of claim 1 in which wool fat is the emulsifier.

3. Pharmaceutical composition of claim 1 in which wool wax alcohol is the emulsifier.

4. Pharmaceutical composition of claim 1 in which salts of pharmacologically permissible metals with aliphatic monocarboxylic acids with ten to 22 carbon atoms is the emulsifier.

5. Pharmaceutical composition of claim 1 in which mono- and/or di-glycerides of aliphatic monocarboxylic acids with ten to 22 carbon atoms are the emulsifier.

6. Pharmaceutical composition of claim 1 which consists essentially of about fifty percent by weight of coconut oil, thirty percent by weight of palm kernel oil, ten percent by weight of laurel oil m.p., approximately 36° C. and ten percent by weight of wool fat.

7. Pharmaceutical composition of claim 1 which consists essentially of about forty percent by weight of coconut oil, forty percent by weight of palm kernel oil, ten percent by weight of laurel oil m.p., approximately 36° C. and ten percent by weight of zinc stearate.

8. Pharmaceutical composition of claim 1 which consists essentially of about fifty percent by weight of coconut oil, thirty percent by weight of palm kernel oil, ten percent by weight of laurel oil m.p., approximately 36° C. and ten percent by weight of zinc stearate.

9. Pharmaceutical composition of claim 1 which consists essentially of about thirty percent by weight of coconut oil, fifty percent by weight of palm kernel oil, ten percent by weight of laurel oil m.p., approximately 36° C. and ten percent by weight of zinc stearate.

10. Pharmaceutical composition of claim 1 which contains from 0.01 to 0.2 percent each by weight of a preservative and an antioxidant, the percentages by weight summing up to 100 percent.

11. Pharmaceutical composition of claim 1 in which the extract of laurel (*Laurus nobilis* (Linn.)) consists of a mixture of fifty to 100 percent by weight of laurel tallow m.p. about 40° C. and fifty to 0 percent by weight of laurel oil m.p., approximately 36° C., the percentages by weight summing up to 100 percent.

12. A method for the external treatment of psoriasis, tinea and eczema, comprising the repeated topical application, to the affected dermal site, of a therapeutically effective amount of a composition of claim 1.

* * * * *

UNITED STATES PATENT AND TRADEMARK OFFICE
CERTIFICATE OF CORRECTION

PATENT NO. : 4,235,889
DATED : November 25, 1980
INVENTOR(S) : Walter Evers

It is certified that error appears in the above-identified patent and that said Letters Patent are hereby corrected as shown below:

Col. 2, line 14; "Ullmans" should read -- Ullmanns --
Col. 10, line 18, (second column with heading "Ca"); "+ ♂" should read -- 30 ♂ --
Col. 10, line 53; "patents" should read -- patients --

Signed and Sealed this

Sixteenth Day of June 1981

[SEAL]

Attest:

RENE D. TEGTMEYER

*Attesting Officer*     *Acting Commissioner of Patents and Trademarks*